United States Patent [19]

Harvey et al.

[11] Patent Number: 4,690,001

[45] Date of Patent: Sep. 1, 1987

[54] OPTICAL DISPLACEMENT TRANSDUCER USABLE AS AN EXTENSOMETER

[75] Inventors: Dennis N. Harvey, Chaska, Minn.; Robert B. Bertolasi, Rockford, Ill.

[73] Assignee: MTS Systems Corporation, Eden Prairie, Minn.

[21] Appl. No.: 797,435

[22] Filed: Nov. 13, 1985

[51] Int. Cl.⁴ .............................................. G01L 1/24
[52] U.S. Cl. .................................. 73/800; 358/213.11
[58] Field of Search ............... 73/87, 800; 250/231 R; 358/213

[56] References Cited

U.S. PATENT DOCUMENTS 4,574,642 3/1986 Fleischman ....................... 73/800 X

OTHER PUBLICATIONS

MTS Systems Corporation product brochure, Optical Extensometer, Product No. 926.44, 1983.
Appendix B Operation Manual, Digital Camera Operation, published 1983, (approximately).
Brochure "Image Sensing Systems By Reticon", published in 1979.

*Primary Examiner*—Eugene R. Laroche
*Assistant Examiner*—Steven J. Mottola
*Attorney, Agent, or Firm*—Kinney & Lange

[57] ABSTRACT

A non-contact, displacement transducer (optical extensometer), which is relatively simple to make and operate, and therefore low cost, utilizes 35 mm camera optics for the lens system and will focus a beam of light along a linear path of light sensitive elements representing a gauge length of a specimen or member. Flags or similar indicators that change the pattern of the light beam are mounted or marked on the specimen at two spaced loations. As the specimen is loaded, the flags will change in spacing, and, as shown, the change in the location of shadow will cause changes in the affected light sensitive elements which provide outputs that indicate displacement in the specimen. The sensing circuitry providing the output is compact and easily mounted within a module carrying the lens. The module may be mounted directly to a test specimen frame.

7 Claims, 7 Drawing Figures

OPTICAL DISPLACEMENT TRANSDUCER
USABLE AS AN EXTENSOMETER

BACKGROUND OF THE INVENTION

1. Field of the Invention

The present invention relates to a displacement transducer for use, for example, as an optical extensometer.

2. Description of the Prior Art

Optical extensometers have been advanced in the prior art, but generally they require quite complex optical systems, and light sensor systems. The present device is designed to simplify the optical requirements and provide very acurate results.

Other types of non-contact extensometers have been capacitive type, but a digital output is desired in extensometers, and the present device includes means for providing a direct digital display and buffered digital data for outputs.

SUMMARY OF THE INVENTION

The present device relates to an optical displacement transducer, as disclosed, an extensometer which uses a solid state, one dimensional array of light sensitive elements, wherein the light zones are focused with standard 35 mm camera lenses, and which will receive light that is directed onto a specimen to be tested to determine the relative location of light affecting indicators mounted along the length of the specimen, and that are positioned between the light source and the light array.

The circuitry is easily mounted in a small housing carrying the lens, and the housing can be mounted directly to the test frame. The circuitry provides outputs that can be used for driving computers, XY recorders, or oscilloscopes as desired. Additionally, self-contained digital display, and a direct visual display of light and shadow representing the pixels, are provided for rapid checking.

The device is made so that it can measure using a dark zone with light borders, or a light zone with dark borders, depending upon selection of the operator. The operator may select zones for the output signal that are within the field of view, to make sure that the area of interest is being examined.

DETAILED DESCRIPTION OF THE PREFERRED EMBODIMENTS

Figure 1:
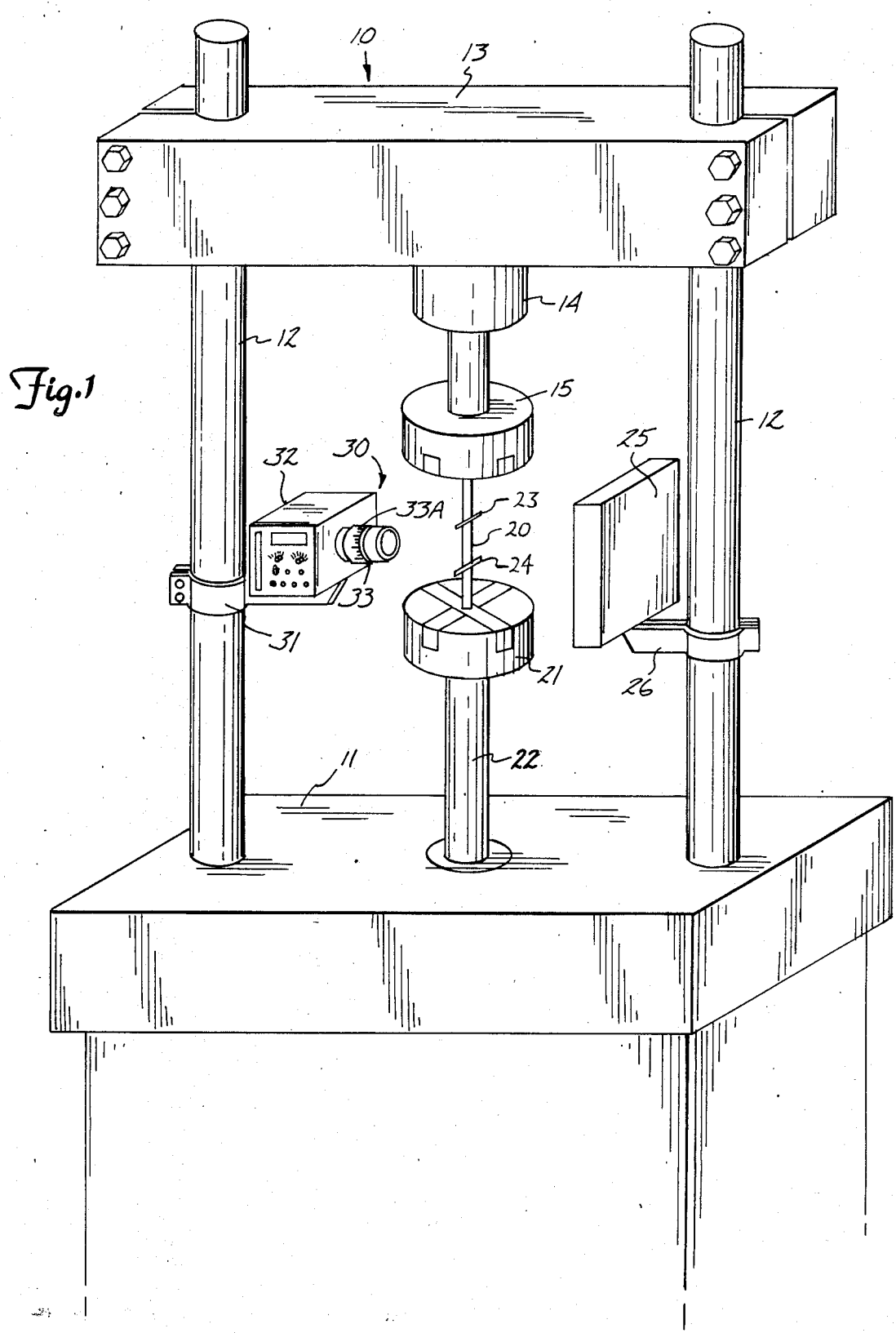
FIG. 1 is a perspective view of a typical test setup, utilizing an optical extensometer made according to the present invention.

A typical test set up is illustrated in FIG. 1 and includes a load frame 10 which has a base 11, and upright columns 12, 12. A cross head 13 is adjustably clamped on the columns 12, 12 in a suitable manner, and the cross head supports a load cell 14, and through the load cell supports an upper specimen grip 15 of conventional design. A specimen indicated generally at 20 is held in the upper grip 15 and in a lower grip 21, which in turn is connected through an actuator rod 22 to a suitable hydraulic actuator that will apply a load to the specimen. The load is usually a tensile load.

The specimen 20 has a pair of clip-on flags or opaque indicators that are suitably coupled to the specimen. There is an upper specimen clip or flag 23, and a lower specimen clip or flag 24. These are opaque, so that they do not transmit light.

As the specimen 20 is loaded in tension, for example, the flags 23 and 24 tend to separate as the specimen is loaded. Rapid indication of any change is desirable. While the specific disclosure herein will deal with shadow casting or shadow forming flags, the clips can be replaced with light reflecting spots or light reflecting members on the specimen, and upon use of a light source in the proper position, the definition between lighter and darker areas will be accomplished in the same manner as that which will be disclosed.

As shown, a light source or light box, indicated generally at 25, is mounted onto a support 26 that is clamped onto one of the test frame columns 12, and is positioned on the first side of specimen 20. An optical extensometer sensor, indicated generally at 30, is mounted with a suitable support 31 onto the other one of the columns 12 of the load frame.

The optical extensometer sensor 30 comprises a suitable housing or box 32 mounting a lens 33 that has a focal length so that its field of view will span the length of the specimen 20; that is, it is sufficient to extend beyond the upper and lower edges of the flags or clips 23 and 24. The lens is a standard, adjustable-focus camera lens for a 35mm camera, having a focusing adjustment ring 33A.

Figure 2:
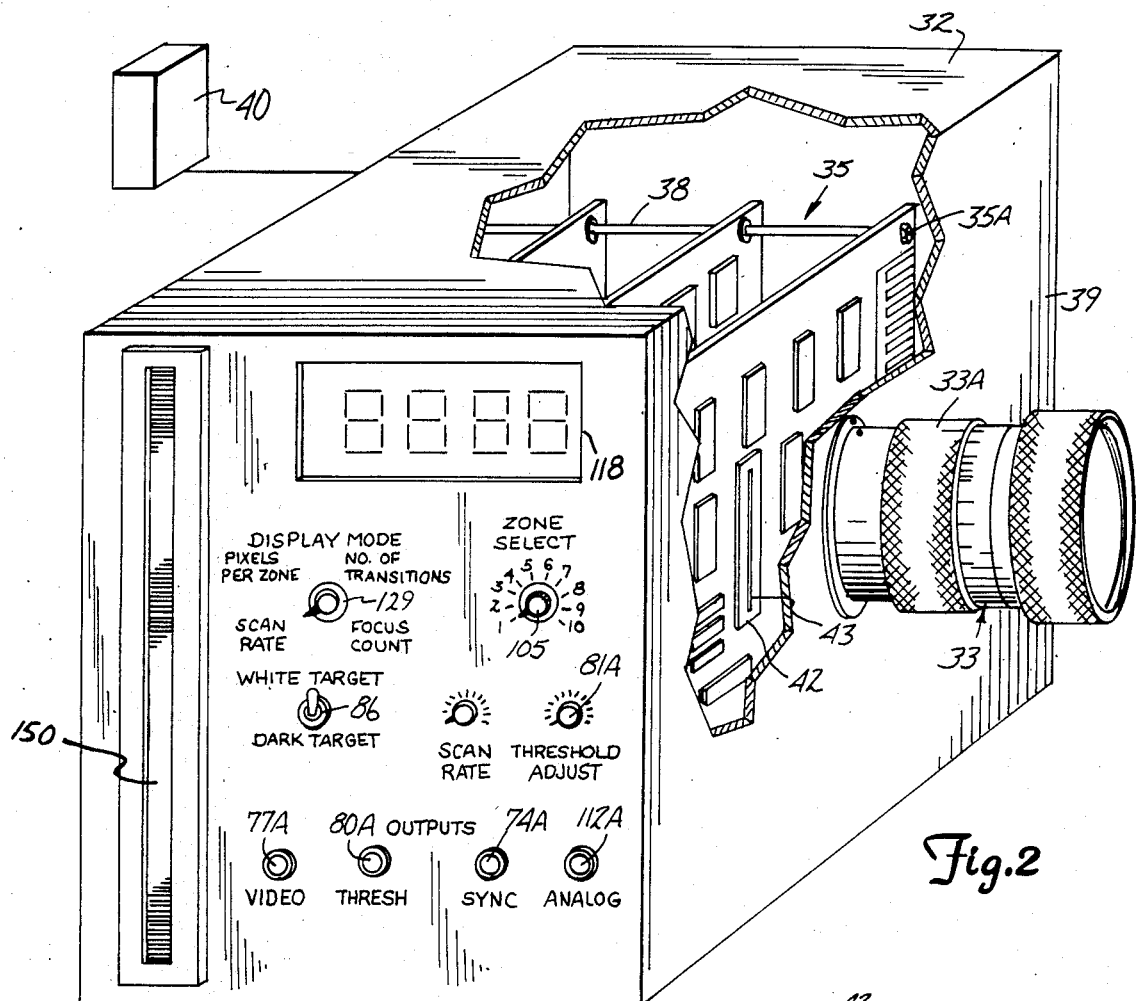
FIG. 2 is a perspective, fragmentary view of an optical extensometer housing for mounting a lens and housing the sensing circuitry according to the present invention.

As shown in FIG. 2, the box 32 forms a housing that has an interior in which a plurality of circuit boards or cards, indicated at 35 generally, are mounted on a suitable support 38. (There can be one such support in each corner of the circuit boards or cards.) The front wall 39 of the housing 32 supports the lens 33, and the first of the circuit cards indicated at 35A immediately behind the lens has a linear array of light sensitive elements indicated generally at 42 thereon. The elements are, as shown, photosensitive diodes that are divided up into individual pixels, and each of the pixels will provide an electrical signal that is indicative of light on that particular pixel. Because the linear array, which is represented by the linear line 43, is divided into these individual pixels or cells, the location of transitions between light and dark along this line can be detected by suitable detecting means. Typically the array will be either 1024 or 2048 pixels.

Figure 3:
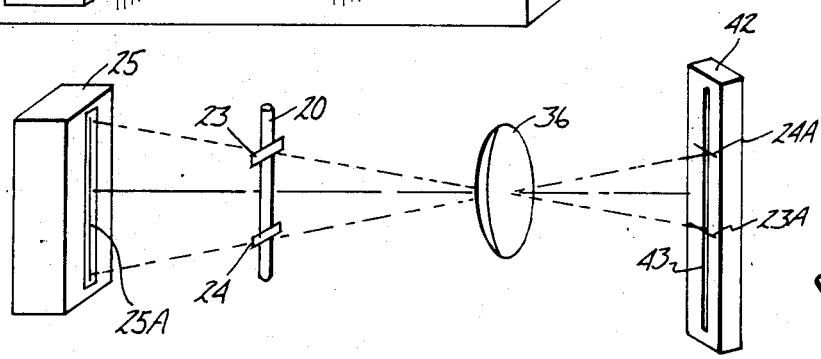
FIG. 3 is a schematic representation of the data path of the device of the present invention.

FIG. 3 is a schematic representation of the data path, and includes the light box 25, which provides a light beam indicated generally at 25A that is directed toward the specimen 20, with the top and bottom clips 23 and 24 shown in place. The lens 36 is represented, and it focuses the light onto the board 35A and along the detector array 43. The line 43 is illustrated in FIG. 3, and the shadows from the clips 23 and 24 are shown at 23A and 24A, respectively. The individual pixels are identified as to their positions along the length of a line 43, and are coupled to provide a video voltage signal that has a level indicating whether the pixel is in light or shadow.

Figure 4:
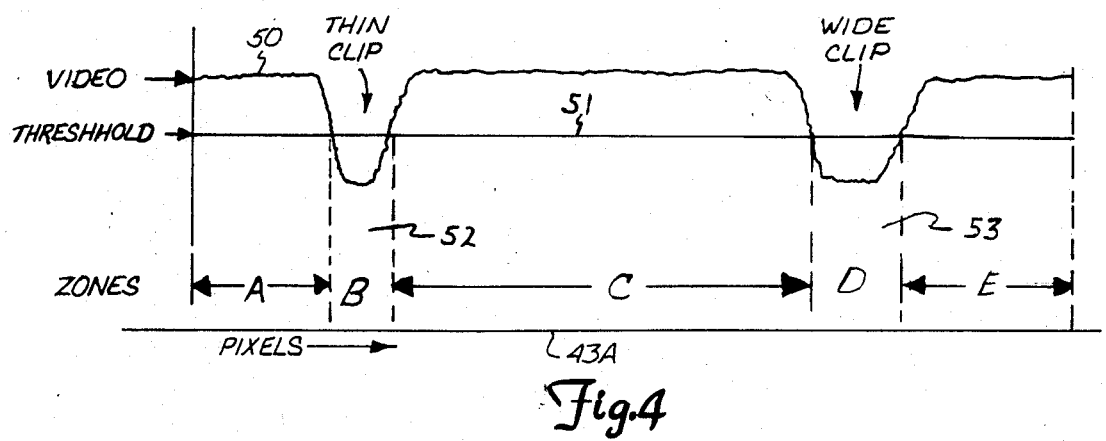
FIG. 4 is a graphic plot of signals delivered by the device of the present invention.

In FIG. 4, a plot of the electrical characteristics of the pixels in the linear array is shown. The pixel or individual photosensitive diode number in sequence from the top of the array 42 is represented by the horizontal line 43A, with increasing numbers toward the right. The vertical line in FIG. 4 represents voltage. The voltage level of pixels is line 50 and a threshold voltage level is represented at 51. The output from each pixel or photosensitive diode is established at a level above the threshold when light strikes each of the pixels as represented by line 43A in FIG. 4 as the horizontal line.

In the region shown at 52, the shadow of a clip such as 23A will cause the output on the pixels in the shadow to drop in voltage below the threshold level to the lower level, and the second clip, which is shown as a wider clip for illustration, will cover more pixels and the wider area is indicated at 53. This region represents the pixels that are in shadow, which causes a voltage drop in the shadow area 24A.

The line 43a is divided into sensing zones by the points at which the pixel voltage (video) crosses the threshold voltage. These are indicated as zone A, zone B, zone C, zone D and zone E in FIG. 4. The zone of interest, which will indicate the distance between the clips, is zone C, and the output of the unit is determined by the number of pixels that are in the zone of interest. The output can be digital or analog. For example, if the line 43A is represented by 1024 pixels, the number of pixels in zone C between the transitions from light to dark (or dark to light) can be counted in that each gives an output, and the number of pixels will determine the analog output voltage level. In the circuitry the pixel array is sampled (scanned) sequentially, and the output from each pixel sensed and counted between transitions.

The "zones" providing the output can be selected with a selector switch, and the rate of scan of the pixels can also be adjusted as desired with a suitable potentiometer leading to the timing oscillator.

It should be noted in FIG. 2 that the transformer and power supply indicated generally at 40 can be mounted on a wall remote from the extensometer sensor housing and light source to simplify the mounting of the essential components on the load frame.

Figure 5:
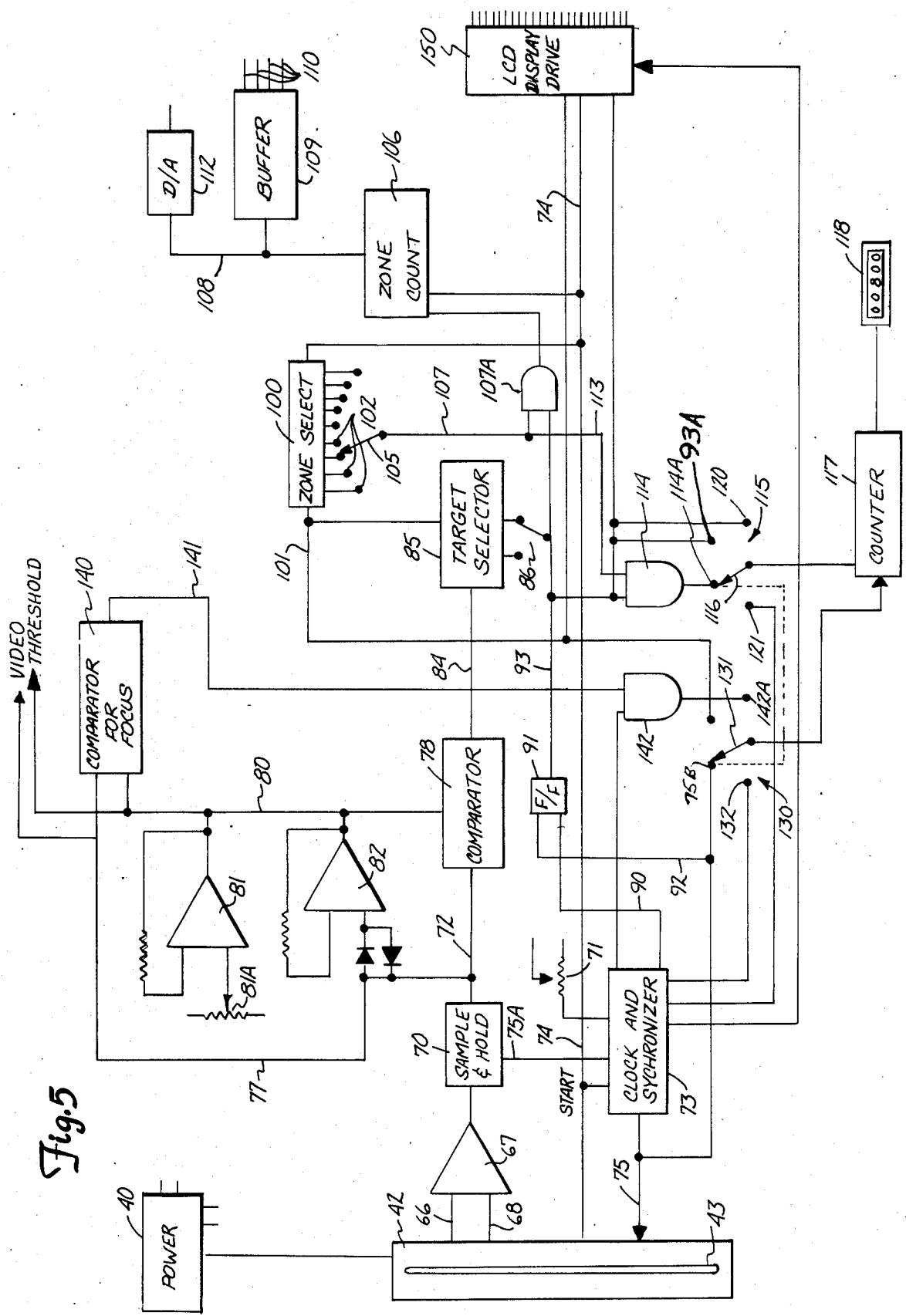
FIG. 5 is a block diagram representation of a typical circuitry used with the present invention.
Figure 6:
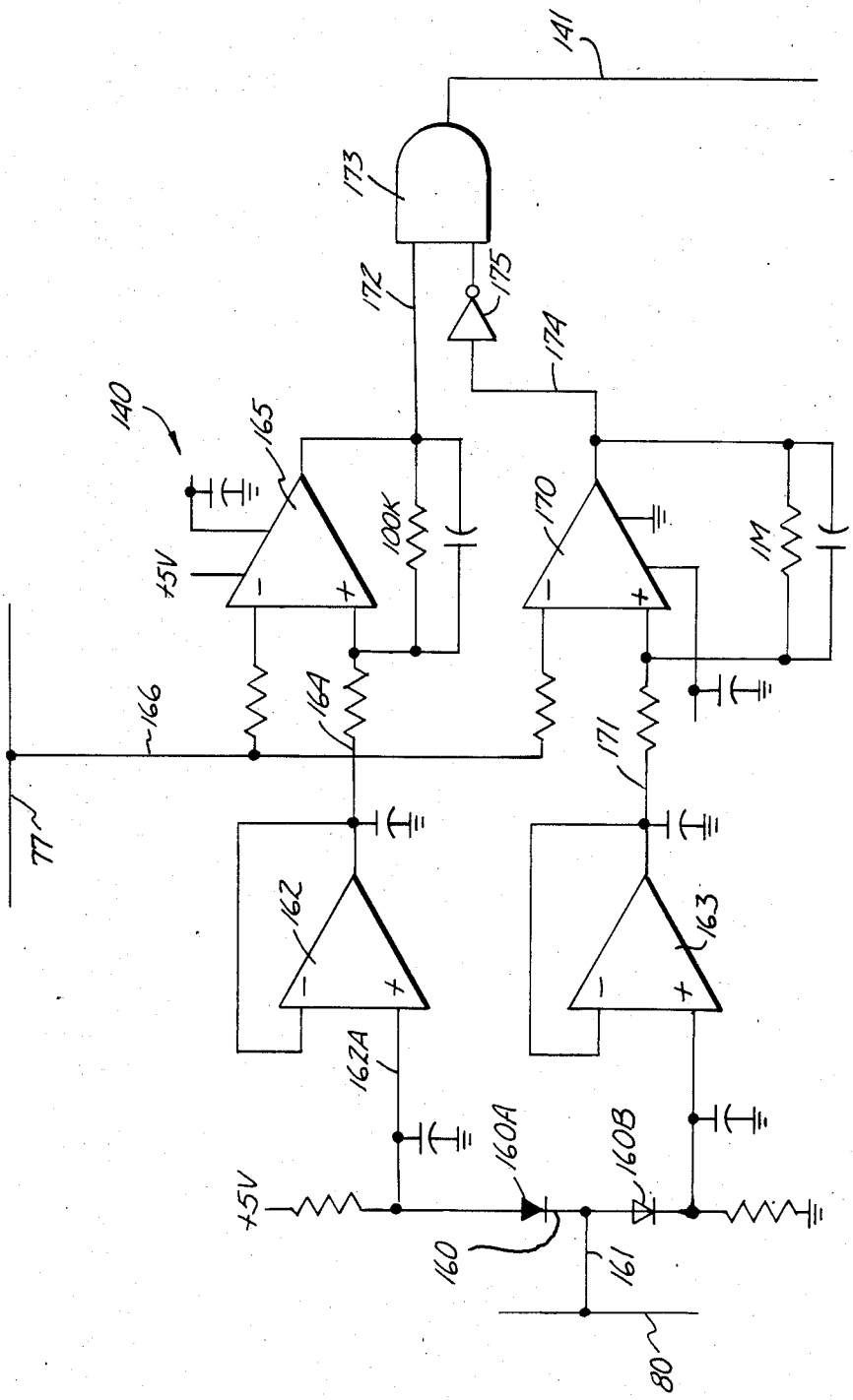
FIG. 6 is a detailed schematic representation of a comparator for the focus count system illustrated in FIG. 5.
Figure 7:
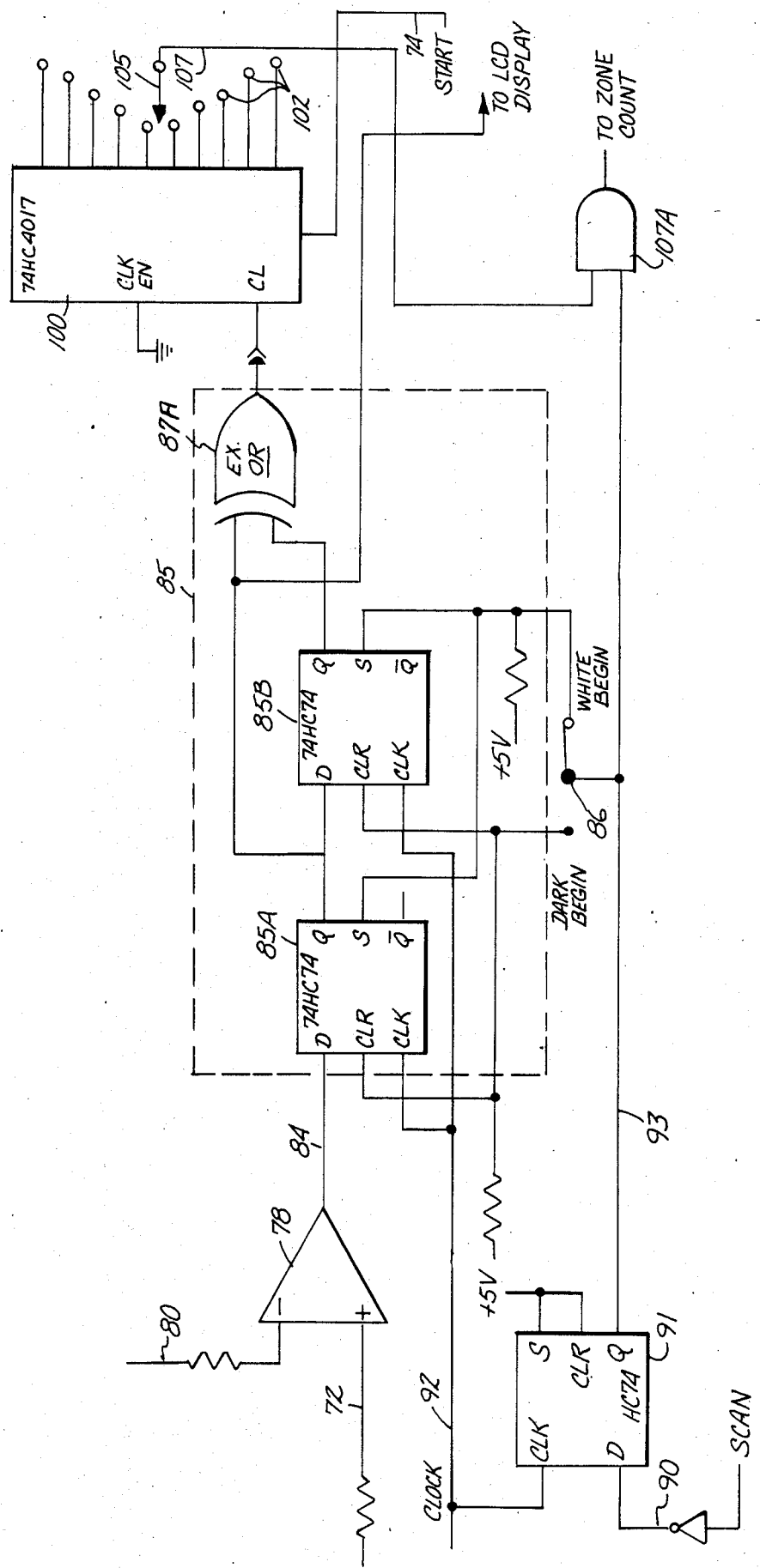
FIG. 7 is a detailed schematic representation of the target selector circuitry illustrated in FIG. 5.

In FIGS. 5, 6 and 7, a block diagram and schematic representation of a typical circuit for utilizing the information obtained by light and dark signals being reflected onto the linear light sensitive array 42 is shown. The light senstive array chip 42 is schematically represented with the line of pixels indicated at 43. The preferred chip is commercially available from Reticon. In the particular form shown, the light sensitive elements are photosensitive diodes, and there are 1,024 such photosensitive diodes (pixels) arranged in the linear line 43 of the array. In actual size, these 1,024 pixels are arranged in a linear line approximately one inch long. When light strikes each photosensitive diode, it will either conduct more current or less current to give an electrical change indicating a change in light. The power supply 40 is used for providing suitable voltage levels for the various components, including a five volt output.

When the photosensitive array chip 42 is powered, it delivers an output from each pixel in sequence along a line 66 to an amplifier 67 that has its other input connected to a reference or set signal on line 68. The amplifier output is proportional to the difference between the reference on line 68 and the signal on line 66. The signal from amplifier 67 is provided to a sample and hold circuit 70 of conventional design, which will sense peak voltages coming from the output of the amplifier 67, and hold the signal level at substantially the peak level for a preselected time, as determined by the scan rate, which is the frequency of the clocking signals. The peak voltage from each pixel is held at a constant level for the time that each of the individual pixels in array 42 is being sensed. The signal along line 72 represents the state of a particular pixel that is being sensed or scanned at that time.

A clock and synchronization circuit 73 of conventional design is used to provide various clocking signals that provide start functions and scanning signals. The circuit also provide blanking signals in a known manner while the scanning goes from the last pixel back to the start, or first pixel. The start signal is provided along a line 74 to the chip 42, to start the sequence of scanning the pixels from top to bottom, and a scanning or clocking signal is provided along line 75 at a desired rate. Each time a clock signal is provided along line 75 (the clock signals repeat at a set rate), the chip 42 will change the output on line 66 to the next pixel in sequence. In other words, the signal on line 66 sequentially shows the state of each of the pixels on the chip 42 at a desired rate. A clock signal 75A at the same rate as that on line 75 but time displaced by approximately 500 nanosec., is used with the sample and hold circuit so that each time a new pixel is being sensed, and its output is on line 66, the sample and hold circuit will be again operable to hold the voltage level for that pixel delivered by the amplifier 67. The start signal on line 74 can be used for a "clear" or a "start" so that there is a synchronization as to the start of the pixel scanning that is provided for the rest of the circuitry. This signal also is provided at a "sync" jack 74A on the housing 32 for synchronizing other components, if desired.

In the particular form shown, the output on line 66, and thus the output from the amplifier 67, is high when the pixel is in light, and if the pixel is in shadow or dark, the output will be low.

The held signal on line 72 is provided to a video signal line 77, which may go to various components, and provides a video output indicating the presence or absence of light on the pixel being sensed. It is provided at an output jack 77A on housing 32 as a video signal for showing that light is present at a particular pixel, and by synchronizing with the scan rate or clock signal on line 75, the state of the pixel can be displayed wherever desired.

This signal from the sample and hold circuit is also fed by line 72 to a comparator 78. Comparator 78 compares the signal on line 72 with a signal on a line 80 which is at a threshold level. The threshold level voltage is a voltage that is provided in a conventional way from an adjustable threshold amplifier 81. The output of the amplifier 81 is summed with a signal from a dynamic threshold amplifier 82. The comparator 78 determines whether or not the voltage level on line 72 is above or below the desired threshold level, which is shown in FIG. 4 by line 51.

The dynamic threshold amplifier is coupled to the line 72, and will provide a small voltage to line 80 that will either add or substract from the voltage provided by the threshold amplifier 81. It can be seen that the threshold amplifier 81 has an adjustable potentiometer input 81A that can be utilized for adjustment of the threshold level. The threshold level is provided at an output jack 80A on housing 32.

If there are a number of pixels in a row that have a high output, the dynamic threshold amplifier will add to the set level from amplifier 81, to build up the threshold level on line 80, and raise it slightly so that the comparator becomes more sensitive to a change from light to dark. In other words, the threshold level will rise. If there are a series of dark pixels, so that there is a low voltage on the sample and hold output line 72, and line 77, the threshold level will decrease so that there will be sensitivity to a shift to high voltage indicating light.

When the voltage on line 72 is above the comparator level, the output from comparator 78 along line 84 will be high, and when it is below the threshold level it will be low. The signal will be fed to a target selector circuitry 85, and essentially the target selector circuitry is to provide a switch function with a switch 86 for determining whether the circuitry is to be preconditioned for processing a light target or a dark target.

As the switching of pixels or sequencing of pixels in the array goes from the last one of the array to the first one of the array, there are generally about 10 to 15 counts of the clock signal provided to make the sequence. The switch 86 will also provide a signal that will keep the target selector pre-conditioned for a light or dark signal start from the sample and hold circuit until pixel No. 1 in the array is again being sensed. Essentially, the voltage levels that are present at the end of the array will not cause a target signal change during the transition from the last pixel to pixel No. 1. Without the signal from the switch 86 there would be a signal indicating a transition from a light zone to a dark zone, when in fact it would be at the same state (light or dark) as the last pixel in the array. For example, if one has a dark target, that is a shadow is being cast by the flags as shown herein, at the end of the array there would be light on the last pixel. Placing switch 86 to provide a light region signal during the sequencing from the last pixel (No. 1024) to the first pixel (No. 1) will cause the displays and necessary components to maintain the output indications at the light region state until the first pixel is again sensed.

The switch 86 will be in either light state or dark state, depending on the target set up, and would remain that way for each individual test set up. The only time that it would be changed is if a light reflecting or light slit target was used instead of a shadow casting flag.

The circuitry 85 will be provided with this signal from switch 86 to hold the output of circuitry 85 in the same state until the comparator 78 signal is again operative. The time that the signal from switch 86 is effective is determined by a count output on a line 90 to a suitable flip flop 91, that also receives a clock signal on line 75 through a line 92, and provides an output on line 93 that will remain the same from pixel 1024 to the start of the next sequence at pixel 1.

The switch 86 is not necessary if the same target system is going to be used all the time because the circuitry 85 could be held to provide a nontransition signal directly during the counts between pixel 1024 and pixel 1. In most instances, the number of these counts to reset the sensing circuitry will be between 10 and 15 clock counts from pixel 1024 to pixel 1.

A zone selector counter circuit indicated generally at 100 (a 74HC4017 circuit) receives a signal from a line 101 on the output of the circuitry 85 each time there is a change in the comparator signal. Once initiated, the zone selector circuit provides an output that is high to one of a plurality of output terminals indicated generally at 102. There is always a high signal at one of the output terminals when the circuit 100 is powered. The high signal appears at each output terminal, sequentially, each time there is a change in state on line 101. After the start signal from line 74 has reset the zone selector to initialize it, the output on line 101 will cause the output on the first terminal (the left-most) to remain high until there is a change in state on line 101. Then, the output on the first terminal will go low and the output on the next terminal, in sequence from left to right in FIG. 5, will go high. This next terminal will remain high until the state of the signal on line 101 goes from high to low, or from low to high. A change in state shows that the signal on line 72 has changed from above the threshold level, as determined by comparator 78, to below the threshold level or vice versa. With each of the changes there will be a sequential shifting from each of the output zone indicator terminals 102 to the next one. The signal from switch 86 is merely to maintain the output signal on line 101 while the scan is sequenced from pixel 1024 to pixel 1. These counts are similar to blanking signals used in television circuits.

A manual zone selector switch 105 is utilized for selecting one of the terminals 102 which would be for a particular zone of interest. For example, referring to FIG. 4, the zones are indicated in the lower line as zones A-E. The zones are defined by the crossing of the threshold voltage level, which changes the state of the comparator 78. The zone of interest can be determined from a visual display, and generally it would be zone C that is the zone of interest because it would show the number of pixels present between the edges of the shadow casting flags. The change in length of the specimen under strain changes the count of pixels between the flags. However, other zones could be of interest, and the zone can be manually selected with the switch 105 in order to determine the distance between transition points where the voltages from the video output signal on line 72 cross the threshold level.

Assuming that the switch 105 is set to zone C, as shown the output signal then will be high when the zone selector circuitry has been sequenced up to the third output terminal 102. Again, this sequential switching occurs in the chip each time there is a change of value (a digital one or zero) on the line 101. After the start signal has been received on line 74, the value on line 101 would be high because the target selector circuit 85 provides a high signal when set for processing dark targets (switch 86), and will continue high as long as the comparator 78 output is high, indicating light is striking the pixels connected to line 66. A high signal would be present on the zone A terminal from circuit 100. A change would occur at the end of zone A when the output from the sample and hold circuit dropped below the threshold level. This will automatically cause a shift on the zone select circuitry 100 to provide the high output on the second terminal 102, and when the output on line 101 again crosses the threshold level positively at the end of zone B, as shown in FIG. 4, there will be another shift to zone C in the zone select circuitry 100, and the output on the third terminal is then high. The transitions across the threshold clock or shift the high output signal to a different one of the output terminals 102 as the transition occurs.

With the zone select switch 105 set to the third terminal 102, when there is a high signal on the zone select switch, which is only during the time that the sensing is at zone C, that is, between the flags, the high signal is provided on line 107, through an AND gate 107A, which is operative when the signal on line 93 is high to a counter indicated at 106, which will count the number of clock pulses on line 75 during the time that this terminal (the third terminal 102) stays high. This count will remain in the counter even after the end of zone C, when the signal on the third terminal 102 goes low, (and the next terminal 102 goes high). The signal provided on line 107 from the switch 105 will be low. This count then provides the number of pixels that are in zone C, and that indicates the distance between the flags.

The count is a digital count that can be provided on a line 108 to digital buffers 109, to provide an output digital value along the output lines indicated at 110 directed to a digital computer or processor for use, or the signal on line 108 can be fed to a digital to analog converter 112, which provides an analog output that is proportional to the number of pixels that are counted during the particular time that zone C is being sensed. An output jack 112A is provided from converter 112 on the housing 32. This provides the primary output of the extensometer.

The signal from the switch 105 is also fed along the line 113, and will provide a high output when a particular zone is selected, through an AND gate 114, to a terminal of a switch 115 that is a two pole switch having a contact arm 116 and including a portion 130 having a contact arm 131 that moves with contact arm 116 to four terminals in each section. With switch 115 in its second position, wiper 116 is connected to terminal 114A, and wiper 131 is connected to terminal 75B. This is the "pixel per zone" count position. When the pixels are in light, and the shadow casting flags are used, both the signal on line 113 and the output signal on line 93 from the flip flop 91 that is fed to the AND gate 114 will be high. A high signal will therefore be present on terminal 114A of switch 115. The switch wiper 116 is connected to terminal 114A, and this high signal will be fed to a counter 117 to enable the counter, which in turn will provide the count from clock 73 to a digital display 118, as the contact arm 131 is in the second position also, so the number of pixels in zone C will be displayed on the digital display 118. The count will stop when the zone select circuit is shifted.

The second switch section 130 permits selection of four different types of information through the digital counter 117 and display 118. When the wiper 131 of this switch is provided to the first terminal 132 to the left (wiper 116 will also move to the left most terminal where a counter enabling clock signal is provided from the circuit 73), the scan rate is displayed on the digital display 118, which is the rate at which the pixels are being scanned in chip 42. The selection of position of switches 115 and 130 is made with a knob 129 on the outside of housing 32 as seen in FIG. 2.

The next terminal to the right of switch 130 is connected to the clock output as stated, and contact arm 116 is also connected to the enabling output terminal 114A of AND gate 114 which provides an enable signal to display the number of pixels in the particular selected zone, when set to this position. The digital output display 118 will display the count of clock signals which occurred on line 75 during the enabled period (zone), and this will be remeasured each time the zone selected with zone select switch 105 is indicated by circuit 100. The next terminal to the right on the switch section 103 is connected to display the number of transitions or changes at the output of target selector circuit 85, by coupling the counter 117 to the input of circuit 100, and to the enabling signal on line 93 through switch wiper 116 and terminal 93A.

The last terminal 142A to the right on switch 130 is connected to a comparator 140 through and AND gate 142 for determining the focus of the lens. Comparator circuit 140 provides a comparator network that senses two threshold levels, one higher and one lower. The circuit 140 is shown in FIG. 6, and senses the threshold from comparator 81 and from the video output signal line 77. The circuit 140 provides a high output along a line 141 during the time the voltage level of the video output signal on line 77 is at a level between the threshold or reference levels set by internal amplifiers of circuit 140, shown in detail in FIG. 6, and as will be more fully explained. The signal on line 141 is connected through one input of AND gate 142, which has its other input connected to a clock signal line from circuit 73 to provide a count output while there is a high signal on line 141. This will provide a count of the number of pixels during the time the signal on line 141 is high, which will indicate the slope of the transition line shown in FIG. 4. This will indicate the focus of the light. If the light band is rather broad and in poor focus, the slope of this line (the number of pixels in horizontal direction) will be greater. If the lens is in very sharp focus the voltage change plot will be almost vertical (very few pixels). This count will appear on the digital counter 118. The focus of the lens is provided by comparing the output voltage on line 77 with two thresholds to provide a count when the video output signal is between the threshold levels. By selecting the switch 130, this count can be determined to give an indication of the focus of the light, and the value can be observed while the focus of the lens is adjusted. The lens is a standard camera lens, as explained, including a focus adjusting ring 33A.

Additionally, a visual LCD display device indicated at 150 is provided, and is shown on the side of the box. The LCD display device has various zones represented on it. For example there may be 256 LCD cells in display 150, that will be placed in a line. The LCD cells are connected so that the 1024 pixels will be divided up, and four pixels are connected to each LCD cell. The first four pixels will be related to the first cell or light of the LCD display device, and so on, and if any one of the pixels of the first four are in a light zone, the output of the first cell of the LCD display device also will be lighted. The LCD display is clocked to scan in synchronization with the pixels, and will then provide a display, such as that shown in FIG. 2, that will indicate light zones and dark zones directly. This signal provides a visual light and dark array of the LCD cells as indicated. The lights are held on during the scanning of the pixels to provide a steady visual display. Again, if any one of the pixels that are associated with one of the cells of the LCD display device is high, that output will be high or light on the unit 150.

In FIG. 6, a detailed schematic representation of the comparator for the focus count is illustrated. The comparator 140 has an input line 160 coupled from a plus five volt source to ground through a pair of resistors and a pair of diodes 160A and 160B. The reference voltage line 80 is connected through a coupling line 161 to line 80 between the diodes 160A and 160B. A first buffer amplifier 162 has its input coupled to line 160 between the first resistor and the input side of diode 160A through a line 162A, and the input side of diode 160A through a line 162A, and the input of a second buffer amplifier 163 is connected to line 160 between the diode 160B and the second resistor. The signal on line 161 will affect the input voltage to the buffer amplifier 163. The output of buffer amplifier 163 is thus a function of the threshold voltage on line 80.

The first buffer amplifier 162 has an output line 164 connected to the positive input of a comparator amplifier 165, and the negative input of this comparator amplifier 165 is connected through a line 166 to the video signal line 77 from sample and hold circuit 70. A second comparator amplifier 170 has its positive input connected to an output line 171 of the second buffer amplifier 163, and the negative input of comparator 170 is also connected to the video signal line 77 that comes from the sample and hold circuit 70.

The comparators 165 and 170 are identically coupled, except the feedback resistors are of different value, with the buffer amplifier 170 having a one megohm feedback resistor and the buffer amplifier 165 having a 100K feedback resistor.

The output of comparator 165 is connected with a line 172 to an AND gate 173. The output of the comparator 170 is connected through a line 174 and through an inverter 175 to the other input of the AND gate 173. The output of the AND gate 173 is connected to the output line 141. This is the output that indicates that the comparator amplifier circuit 140 is between two threshold levels.

The voltage level on lines 164 and 171 are different, with the voltage on line 164 being higher. A video signal voltage level above the voltage on line 164 will result in a low output on line 172. When the video signal voltage is above the voltage on line 171 (and 164) there will be a low output on line 174, which will be inverted by inverter 175, so that the AND gate 173 will have a low output when the video signal is at its high point. The video signal on line 77 drops, as shown in FIG. 4, when a shadow is cast onto certain pixels (from light to dark), and when the signal on line 77 drops to a level below that of the signal on line 164 (but still above the signal on line 171), the output on line 172 will go high, and the AND gate 173 will have two high signals on its inputs, thereby delivering a high signal on line 141. The high signal on line 141 is combined with a scan rate or clock signal through AND gate 142 (see FIG. 5) so that the focus count of pixels will be delivered when the signal on line 141 is high.

When the video voltage signal on line 77 drops further, below the voltage level of line 171, the output on line 174 from comparator 170 will go high, and the output from the inverter 175 will go low, so that the AND gate 173 will then have a high signal at one input and a low signal at the other input so that the output on line 141 will go low. This will shut off the count through AND gate 142.

As the voltage on line 77 again rises, where there is a transition from dark to light on the opposite edge of the flag, there will be a high signal on line 141 while the voltage on line 77 is rising between the two threshold levels. The count during the time the voltage level on line 141 is high gives an accurate count of the number of pixels scanned between the two threshold levels (at line 164 and 171) sensed by comparator 140. The fewer the pixels counted between the threshold voltage levels, the faster the voltage on line 77 falls or rises, and the sharper the focus of the lens.

In FIG. 7, a more specific representation of the circuit 85, that has the target select switch 86 coupled thereto, is shown. Circuit 85 comprises two 74HC74 flip flops 85A and 85B connected as shown to the output of the comparator 78. The output of comparator 78 comprises one data input. A plus five volt source is connected to the clear terminals of both flip flops 85A and 85B, and to the "dark begin" terminal of the switch 86. The five volt source is also connected to the S inputs or preset inputs, and to the "white begin" terminal of the switch 86. Line 93, as can be seen, is connected to the Q output of flip flop 91, which is an HC74 flip flop, having an inverted scan rate signal coupled to the data input 90, and its clock input is connected to the clock line. The clock inputs of the 74HC74 sections 85A and 85B are also connected to the clock line. The Q outputs of both flip flops 85A and 85B, which comprise circuit 85, are connected through an EXCLUSIVE OR gate 87A to the clock input of the zone count circuit 100. If selector switch 86 is set to "white begin", the outputs of flip flop 85A and flip flop 85B will be set high due to a low input on the S (preset) terminals between pixel 1024 and pixel 1. The output of EXCLUSIVE OR gate 87A will be low at the beginning of a scan. At the first dark transition (light to dark) there will be a one pixel delay between the 'low' state on Q output of flip flop 85A and the low state for Q output of flip flop 85B caused by the serial connection from Q output of 85A and input of 85B in conjunction with a common clock timing. During the resulting one pixel output difference between the flip flops 85A and 85B, a one pixel wide high state at the output of gate 87A resulting therefrom will cause the zone selector counter 100 to increment. This occurs at each transition when the inputs to EXCLUSIVE OR gate 87A differ for one pixel count. The process will repeat for each threshold crossing regardless of whether due to increasing or decreasing video levels. The shift signal to circuit 100 of course shifts the high output to the next terminal 102.

The five volt source connected to the "dark begin" position and the clear inputs of 85A and 85B will prevent spurious noise from affecting these inputs when they are not selected by switch 86. Gate 91 serves to delay the scan signal by one clock period to allow pixel one to be processed before incrementing the zone select circuit. Likewise, the delay from gate 91 holds the shift function active until the 1024th pixel is processed.

The device is easily mounted and used and provides the necessary functions for determining changes in distance between markers on a specimen as well as providing lens focus information.

The use of the present invention is to function as a general displacement transducer for determining relative displacement of two markers or flags. The specific extensometer shown discloses the preferred embodiment.

Although the present invention has been described with reference to preferred embodiments, workers skilled in the art will recognize that changes may be made in form and detail without departing from the spirit and scope of the invention.

We claim:

1. A displacement transducer assembly comprising a support housing, a camera lens mounted on one surface of said support housing and including means for adjustably focusing said lens;
   a linear array of individual light sensitive elements positioned in said housing to receive light transmitted through said lens;
   a light source on the exterior of said housing and providing light through the lens transmitted across at least two target areas that change the light transmission pattern in such location along a length axis;
   means to detect the state of light on each of the light sensitive elements, and to sequentially sample the state of light to provide a light sensitive signal;
   said light sensitive signals comprising a signal that varies from a high level in one light state to a low level in a second light state, the signals being proportional to the amount of light between said first and second light states; and
   means to provide a direct count of the number of light sensitive elements sequentially sampled from the time the signal changes from one light level to a second light level on one light sensitive element indicating the leading edge of one target area, until a subsequent light sensitive element provides a signal indicating a change from the second light level to the first light level to indicate the number of light sensitive elements in said second light level and thereby indicate the focus of the lens by providing the number of light sensitive elements in sequence at the light level corresponding to the light transmission pattern of one of said target areas.

2. The apparatus as specified in claim 1 wherein said target areas comprise opaque flag members mounted on a specimen to be tested for elongation, said flag members being mounted at axially spaced locations on such specimen, said light source being on the opposite side of said flag members from the camera lens and linear array.

3. An optical extensometer sensor assembly comprising a housing, a camera lens mounted on a wall of said housing, a circuit card mounted on the interior of said housing and including an array of individual light sensitive elements arranged in a linear relationship to represent the length of a specimen to be sensed and providing a voltage signal as a function of light striking such elements, said light sensitive elements being repeatably scanned at a desired clock rate;
   an exterior light and dark display mounted on said housing comprising a plurality of light emitting elements which provide light in response to a voltage signal and arranged in linear array, and;
   a separate plurality of adjacent ones of said light sensitive elements being coupled to each one of the light emitting elements at corresponding locations on the array and display to provide a light signal on the display when any one of the light sensitive elements coupled to a light emitting element produces an output signal above a threshold level to provide a visual display external of the housing of the conditions of the light sensitive elements.

4. The apparatus of claim 3 including means for providing an indication when the condition of the light sensitive elements changes with respect to a reference level, and for providing a count of the number of light sensitive elements between each of the changes of condition with respect to the reference level.

5. An optical displacement transducer for a use in connection with determining displacement of a pair of targets that are relatively movable with respect to each other, including a light source projecting light and the targets causing a change in light characteristics;
   an optical sensor assembly including a lens to receive light from said light source and project said light onto a light sensitive array that represents a length related to the distance between the targets;
   said targets providing at least two areas of different condition light transmitted through said lens onto said array to indicate two spaced locations for the targets on the array, such light sensitive array comprising a plurality of pixels of light sensitive elements;
   means to sequentially determine the actual voltage level at each pixel in such array, the pixels providing first and second voltage outputs that are different when the light conditions on the pixels are different;
   means for establishing threshold voltages at levels between the first and second voltage outputs representing light and no light condition on the pixels, and for comparing the output voltage of each pixel with respect to the threshold level to provide a comparator output;
   means for counting the pixels between each change of comparator output as the voltage output from the pixels changes and crosses the threshold level; and
   means for adjusting the threshold level voltage as a function of the actual voltage level provided by the pixels as the voltages thereof are sequentially determined.

6. The transducer as specified in claim 3, and zone selection circuit means operable to provide an output representing the number of light sensitive elements scanned in a zone between transititions of the voltage signals from said light sensitive elements across the threshold level, selector switch means on the exterior of said housing to permit manual selection of a zone of interest which is represented on the visual display, and visual indicator means connected to said manual switch means for providing an indication of the number of pixels in the zone selected by the manual switch means.

7. The apparatus as specified in claim 6, wherein said visual indicator means comprises a digital display coupled to said manual switch means for providing a digital number indicating the number of light sensitive elements in the zone selected by the manual switch means, said digital display being mounted on the exterior of said housing adjacent to said exterior light and dark display and said manual switch means.

* * * * *